US012800567B2

(12) United States Patent
Liu et al.

(10) Patent No.: US 12,800,567 B2
(45) Date of Patent: Nov. 17, 2026

(54) ROLLER LUBRICATION PERFORMANCE MEASURING AND TESTING DEVICE

(71) Applicant: Qingdao University of Technology, Qingdao City (CN)

(72) Inventors: Chenglong Liu, Qingdao City (CN); Feng Guo, Qingdao City (CN); Ziqi Xie, Qingdao City (CN); Bin Ju, Qingdao City (CN); Xinming Li, Qingdao City (CN)

(73) Assignee: Qingdao University of Technology, Qingdao (CN)

( * ) Notice: Subject to any disclaimer, the term of this patent is extended or adjusted under 35 U.S.C. 154(b) by 348 days.

(21) Appl. No.: 18/764,673

(22) Filed: Jul. 5, 2024

(65) Prior Publication Data

US 2025/0155425 A1 May 15, 2025

(30) Foreign Application Priority Data

Nov. 14, 2023 (CN) ......................... 202311512742.8

(51) Int. Cl.
*G01N 33/30* (2006.01)
*F16C 13/00* (2006.01)

(52) U.S. Cl.
CPC ........... *G01N 33/30* (2013.01); *F16C 13/006* (2013.01)

(58) Field of Classification Search
CPC ....... G01N 33/30; F16C 13/006; G01M 13/04
See application file for complete search history.

(56) References Cited

U.S. PATENT DOCUMENTS 6,324,899 B1 * 12/2001 Discenzo ........... G01N 33/2888 73/54.02
6,691,551 B2 * 2/2004 Otaki ..................... G01N 33/30 73/9
2022/0050045 A1 * 2/2022 Zhang .................... G01B 5/066

FOREIGN PATENT DOCUMENTS

CN 105783828 B * 10/2018 ............. G01B 21/08
CN 111780972 A * 10/2020 ............. G01N 33/30
CN 109187188 B * 12/2020 ............... G01N 3/08

* cited by examiner

*Primary Examiner* — Francis C Gray
(74) *Attorney, Agent, or Firm* — Pilloff Passino & Cosenza LLP; Rachel Pilloff; Sean Passino

(57) ABSTRACT

The disclosure belongs to the technical field of line contact lubrication characteristic test measurement, and provides a roller lubrication performance measuring and testing device, including a frame and two arc-shaped guide rails arranged in the frame, the frame is arranged on a workbench, the arc-shaped guide rails are slidably matched with the frame, inner arc surfaces of the two arc-shaped guide rails are oppositely arranged, and the two arc-shaped guide rails are fixedly connected; a roller rotatably connected to a bottom one of the arc-shaped guide rail; a contact ring arranged between the inner arc surfaces of the two arc-shaped guide rails; a first driving mechanism used for driving the contact ring to rotate, a second driving mechanism used for driving one of the arc-shaped guide rails to slide relative to the frame, and an image acquisition device used for acquiring oil film images on the surface of the roller.

10 Claims, 11 Drawing Sheets

ROLLER LUBRICATION PERFORMANCE MEASURING AND TESTING DEVICE

CROSS-REFERENCE TO RELATED APPLICATIONS

This application claims priority to Chinese Patent Application No. 202311512742.8, filed on Nov. 14, 2023, the contents of which are hereby incorporated by reference.

TECHNICAL FIELD

The disclosure belongs to the technical field of line contact lubrication characteristic test measurement, and in particular to a roller lubrication performance measuring and testing device, especially being capable of being used to explore the lubrication characteristics under the conditions, such as contact between a cylindrical roller and a bearing flange, roller skew and modification.

BACKGROUND

Cylindrical roller bearings may bear large radial load and are suitable for high-speed and heavy-load operation occasions, such as high-speed machine tool spindles, wind turbines, high-speed train gear boxes, aero-engines, shield tunneling machines and so on.

Because the outer cylindrical surface of cylindrical roller is the main working surface of rolling bearing, the shape accuracy, surface quality and consistency of the outer cylindrical surface will have a great impact on the motion accuracy and working life of the bearing. On the other hand, the lubrication problem between the cylindrical roller and the inner ring guide surface has been puzzling bearing engineers, and people have been optimizing lubrication by means of roller modification, but the actual working state between roller end surface and inner ring/outer ring guide surface after modification has not been directly observed. In addition, the cylindrical roller bearing is separated bearing, and includes an inner ring, an outer ring, a cage and a cylindrical roller. Usually, both the inner ring and the outer ring are designed with flanges to play a role of axial bearing. However, the contact between flange and roller is a difficult problem in the field of tribology. At present, there is a lack of technology to measure the friction force at the contact position between roller and flange, so it is urgent to develop a roller lubrication performance measuring and testing device to solve the above problems.

SUMMARY

An objective of the disclosure is to provide a roller lubrication performance measuring and testing device to solve the above problems and measure the film thickness and the friction torque of line contact of a roller under different conditions.

In order to achieve the above objective, the disclosure provides a following scheme: a roller lubrication performance measuring and testing device, including:

- a workbench;
- a supporting mechanisms including a frame and two arc-shaped guide rails arranged in the frame, where the frame is arranged on the workbench, the arc-shaped guide rails are slidably matched with the frame, inner arc surfaces of the two arc-shaped guide rails are arranged oppositely, and the two arc-shaped guide rails are fixedly connected;

- a roller rotatably connected to a bottom one of the arc-shaped guide rails;
- a contact ring arranged between the inner arc surfaces of the two arc-shaped guide rails, where an outer surface of the contact ring is used for abutting against a surface of the roller, and a front end of the contact ring is provided with a retaining ring for abutting against a side wall of the roller;
- a first driving mechanism, where a driving end of the first driving mechanism is connected with the contact ring, and the first driving mechanism is used for driving the contact ring to rotate, so that the contact ring generates friction with the surface of the roller;
- a second driving mechanism, where a driving end of the second driving mechanism is connected with the bottom one of the arc-shaped guide rails at bottom, and the second driving mechanism is used for driving the bottom one of the arc-shaped guide rails to slide relative to the frame so as to adjust pressure between the roller and the outer surface of the contact ring; and
- an image acquisition device used for acquiring oil film images on the surface of the roller.

In an embodiment, a clamping groove is formed in the bottom one of the arc-shaped guide rails at bottom, and the roller is rotatably connected in the clamping groove.

In an embodiment, the device also includes a positioning shaft group, and an inner wall of the clamping groove is provided with two shaft holes corresponding to the positioning shaft group, where the positioning shaft group includes a positioning shaft penetrating between the two shaft holes, and the roller is rotatably connected with the shaft holes through the positioning shaft, and micro bearings are arranged in the shaft holes corresponding to the positioning shaft, and the micro bearings are used for adjusting an inclination angle of the positioning shaft.

In an embodiment, the contact ring has a transparent structure, and the image acquisition device is arranged in a central hole of the contact ring, and an image acquisition end of the image acquisition device faces the roller.

In an embodiment, the image acquisition device includes an imager for acquiring the oil film images on the surface of the roller.

In an embodiment, the first driving mechanism includes a driving motor, a pair of belt pulleys, a belt sleeved between the pair of belt pulleys, and a transmission shaft arranged on the contact ring, where the transmission shaft coincides with an axis of the contact ring, and one of the pair of belt pulleys is connected with the driving motor, and an other of the pair of belt pulleys is connected with the transmission shaft.

In an embodiment, the first driving mechanism also includes a transmission shaft seat connected with the transmission shaft, and the transmission shaft seat is connected with the other of the pair of belt pulleys through couplings.

In an embodiment, the second driving mechanism includes an oil cylinder, and a driving end of the oil cylinder penetrates through the frame and abuts against the bottom one of arc-shaped guide rails.

In an embodiment, the device also includes a mounting seat fixedly connected to the workbench, and the image acquisition device is movably connected to the mounting seat.

In an embodiment, the workbench includes an upper platform and a lower platform, where the upper platform and the lower platform are fixedly connected through brackets, and a top surface of the upper platform is slidably connected with a mounting plate, and the supporting mechanism is arranged on the mounting plate.

Compared with the prior art, the disclosure has following advantages and technical effects.

According to the disclosure, the inner arc surfaces of the two arc-shaped guide rails are matched with each other to form a test hole duct for supporting the contact ring to extend into the two arc-shaped guide rails and contact with the roller. The roller is rotatably connected on the one of the arc-shaped guide rails at bottom, and the contact ring is driven to rotate in combination with the first driving mechanism, and the contact ring abuts against an outer surface of the roller, thereby simulating a friction situation of the outer surface of the roller in an actual environment. Moreover, the second driving mechanism is connected with the arc-shaped guide rails slidably connected in the frame to control the sliding connection of the arc-shaped guide rails and the frame, driving the roller to move and adjust contact pressure between the roller and a contact surface of the contact ring. According to a film thickness change between an oil film on the surface of the roller and the contact ring under an action of friction force, a friction force change of the roller under different pressures can be known. Finally, the image acquisition device arranged on the workbench obtains the oil film images between the roller and the contact surface, which facilitates the realization of film thicknesses and friction torques of the roller in line contact under different conditions. Moreover, the retaining ring integrally formed at the front end of the contact ring contacts with the side wall of the roller, so that friction occurs between the roller and the retaining ring on the contact ring. The retaining ring is used to simulate a friction situation caused by the contact between the roller and a bearing flange in actual use. By collecting the oil film images generated by the outer surface of the contact ring and the surface of the roller when the roller contacts the retaining ring, the measurement of a contact friction force between the roller and the flange is realized.

BRIEF DESCRIPTION OF THE DRAWINGS

In order to explain embodiments of the disclosure or technical schemes in the prior art more clearly, drawings needed in embodiments are briefly introduced below. Obviously, the drawings in a following description are only some embodiments of the disclosure. For ordinary people in the field, other drawings may be obtained according to these drawings without making creative efforts.

DETAILED DESCRIPTION OF THE EMBODIMENTS

Figure 1:
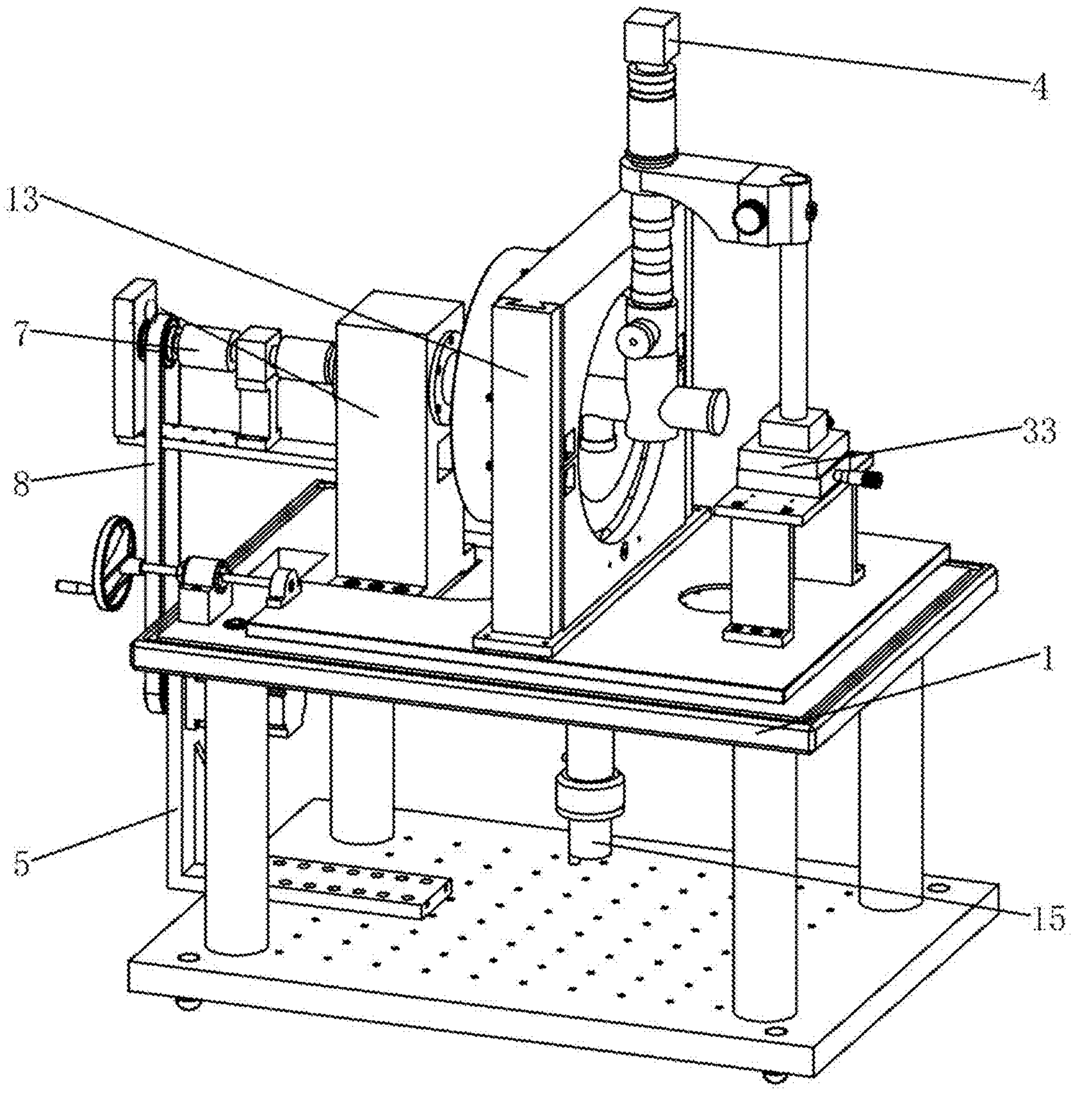
FIG. 1 is a schematic diagram of a main structure according to the disclosure.

In the following, technical schemes in embodiments of the disclosure may be clearly and completely described in combination with attached drawings in embodiments of the disclosure. Obviously, the described embodiments are only a part of the embodiments of the disclosure, but not all embodiments. Based on the embodiments in the disclosure, all other embodiments obtained by ordinary technicians in the field without creative efforts belong to a scope of protection of the disclosure.

In order to make above objects, features and advantages of the disclosure more obvious and easier to understand, the disclosure may be further described in detail in combination with the attached drawings and specific embodiments.

In the prior art, for example, in literature [1] (*Design and preliminary experimental study of roller ring contact type photoelastic flow test device*), the influence of roller modification is indirectly measured through the contact between a roller and an outer ring. An outer ring driving mode is adopted, resulting in problems such as vibration and eccentricity of roller movement under high speed and light load. Literature [2] (*Analysis of friction characteristics of textured inner ring flange of cylindrical roller bearing*) and others improve the friction design of flange by measuring the friction torque of the whole cylindrical roller bearing, but the influence of flange on roller lubrication may not be directly observed. Literature [3] (*Research on isothermal elastohydrodynamic lubrication of skewed roller pair*) mentioned a device for measuring a skew film thickness of a roller. In the scheme, four rollers are used to support a tested roller, leading to a large friction force, which will affect the positioning of the roller and the friction force. There is no friction force measuring part in this literature.

Embodiment: with reference to FIG. 1 to FIG. 11, the disclosure provides a roller lubrication performance measuring and testing device, including:

- a workbench 1;
- a supporting mechanism including a frame 13 and two arc-shaped guide rails 14 arranged in the frame 13, where the frame 13 is arranged on the workbench 1, the arc-shaped guide rails 14 are slidably matched with the frame 13, inner arc surfaces of the two arc-shaped guide rails 14 are arranged oppositely, and the two arc-shaped guide rails 14 are fixedly connected;
- a roller 2 rotatably connected to a bottom one of the arc-shaped guide rails 14;
- a contact ring 3 arranged between the inner arc surfaces of the two arc-shaped guide rails 14, where an outer surface of the contact ring 3 is used for abutting against a surface of the roller 2, and a front end of the contact ring 3 is provided with a retaining ring for abutting against a side wall of the roller 2;
- a first driving mechanism, where a driving end of the first driving mechanism is connected with the contact ring 3, and the first driving mechanism is used for driving the contact ring 3 to rotate, so that the contact ring 3 generates friction with the surface of the roller 2;
- a second driving mechanism, where a driving end of the second driving mechanism is connected with the bottom one of the arc-shaped guide rails 14, and the second driving mechanism is used for driving the bottom one of the arc-shaped guide rails 14 to slide relative to the frame 13 to adjust pressure between the roller 2 and a surface of the contact ring 3; and an image acquisition device used for acquiring oil film images on the surface of the roller 2.

According to the disclosure, the inner arc surfaces of the two arc-shaped guide rails 14 are matched with each other to form a test hole duct for supporting the contact ring 3 to extend into the two arc-shaped guide rails 14 and contact with the roller 2. The roller 2 is rotatably connected on the one of the arc-shaped guide rails 14 at bottom, and the contact ring 3 is driven to rotate in combination with the first driving mechanism, and the contact ring 3 abuts against an outer surface of the roller 2, thereby simulating a friction situation of the outer surface of the roller 2 in an actual environment. Moreover, the second driving mechanism is connected with one of the arc-shaped guide rails 14 slidably connected in the frame 13 to control the slidably connection of the arc-shaped guide rails 14 and the frame 13, driving the roller 2 to move and adjust contact pressure between the roller 2 and a contact surface of the contact ring 3. According to a film thickness change between an oil film on the surface of the roller 2 and the contact ring 3 under an action of friction force, a friction force change of the roller 2 under different pressures can be known. Finally, the image acquisition device arranged on the workbench 1 obtains the oil film images between the roller 2 and the contact surface, which facilitates the realization of film thicknesses and friction torques of the roller 2 in line contact under different conditions. Moreover, the retaining ring integrally formed at the front end of the contact ring 3 contacts with the side wall of the roller 2, so that friction occurs between the roller 2 and the retaining ring on the contact ring 3. The retaining ring is used to simulate a friction situation caused by the contact between the roller 2 and a bearing flange in actual use. By collecting the oil film images generated when the outer surface of the contact ring 3 abuts against the surface of the roller 2 when the roller 2 contacts the retaining ring, the measurement of a contact friction force between the roller 2 and the flange is realized.

Figure 9:
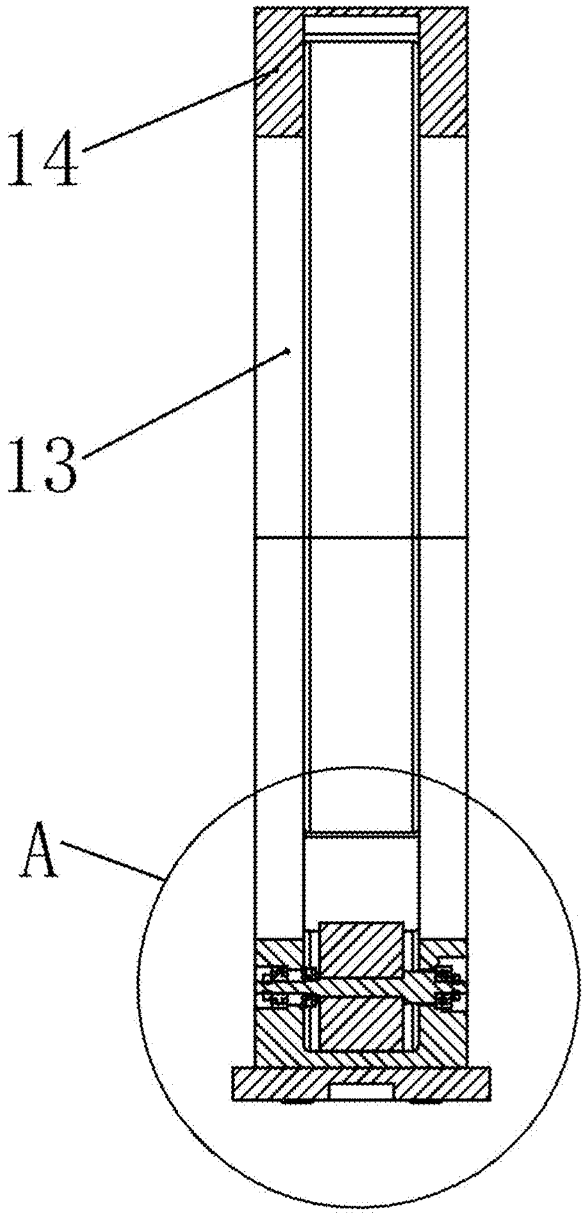
FIG. 9 is a sectional diagram taken along a line A-A in FIG. 8.

With reference to FIG. 1 and FIG. 9, the contact pressure between the roller 2 and the contact ring 3 is adjusted by the second driving mechanism acting on the arc-shaped guide rail 14 and combining with the arc-shaped guide rails 14 sliding in the frame 13. Moreover, the two arc-shaped guide rails 14 are arranged oppositely, and the two arc-shaped guide rails 14 are fixed at mutually close ends of two sides of the two arc-shaped guide rails 14 by using connection methods such as bolts and buckles. By measuring an initial film thickness when the contact ring 3 is not in contact with the roller 2, and measuring a secondary film thickness when a contact end is in contact with the roller 2, a friction torque of the roller 2 is calculated by subtracting the two results. Combined with the first driving mechanism and the second driving mechanism set for the roller 2 and the contact ring 3 and the frame 13, friction tests of the roller 2 under various conditions are realized.

In an embodiment, a clamping groove is formed in the bottom arc-shaped guide rail 14 at bottom, and the roller 2 is rotatably connected in the clamping groove.

In an embodiment, the device also includes a positioning shaft group, and an inner wall of the clamping groove is provided with two shaft holes 17 corresponding to the positioning shaft group, where the positioning shaft group includes a positioning shaft 16 penetrating between the two shaft holes 17, and the roller 2 is rotatably connected with the shaft holes 17 through the positioning shaft 16, and micro bearings 28 are arranged in the shaft holes 17 corresponding to the positioning shaft 16, and the micro bearings 28 are used for adjusting an inclination angle of the positioning shaft 16.

Figure 10:
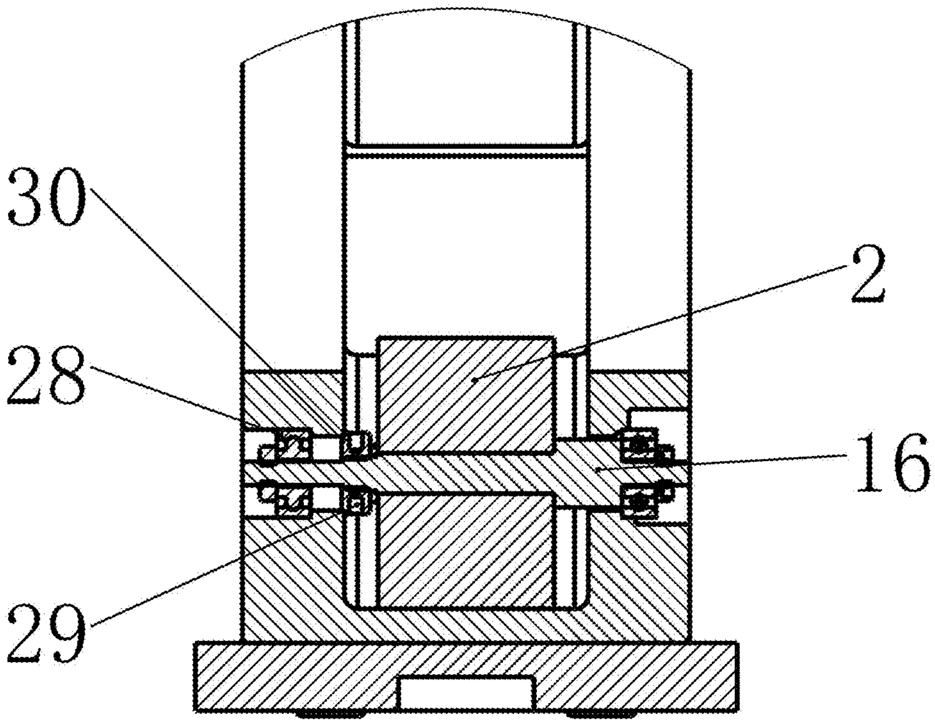
FIG. 10 is a partial enlarged diagram at A in FIG. 9.
Figure 11:
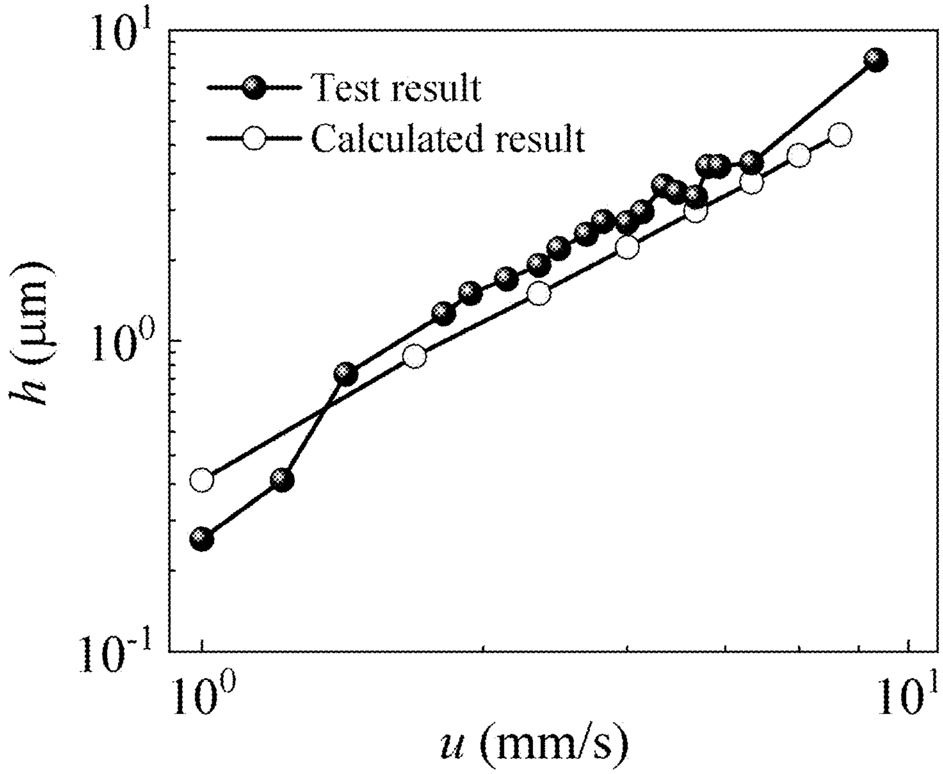
FIG. 11 is a comparison diagram of line contact film thickness test and theoretical results.

With reference to FIG. 9 and FIG. 10, the roller 2 is provided in the clamping groove, and opposite sides of the inner wall of the clamping groove are respectively formed with the shaft holes 17. The positioning shaft 16 is installed by inserting the positioning shaft 16 into the shaft holes 17 and using the micro bearings 28 with different shaft diameters on both sides. An outer ring of the positioning shaft 16 is fixed with inner rings of the micro bearings 28, and an inner ring of the positioning shaft 16 is fixedly connected with the roller 2, while outer rings of the micro bearings 28 are fixedly connected with inner walls of the shaft holes 17, thereby realizing skew deviation of the roller 2 in the clamping groove. By collecting images of a line contact surface between the roller 2 and the contact ring 3, a simulation experiment on the skewed roller 2 is completed, further the simulation data of the measurement experiment is increased and the accuracy of the measurement data is improved. Obviously, when the shaft diameters of the micro bearings 28 on both sides are the same, the roller 2 is horizontally arranged in the clamping groove.

In one embodiment of the disclosure, gap is arranged correspondingly between two sides of the roller 2 and the clamping groove. When the contact ring 3 is in contact friction with the roller 2 in the clamping groove, the retaining ring fixedly connected on a peripheral side of an outer port of the contact ring 3 extends into the gap between the roller 2 and the clamping groove. Spring washers 29 and fastening nuts 30 are correspondingly arranged on the other side, away from the retaining ring, of the roller 2, so that a position of the roller 2 on the positioning shaft 16 may be adjusted, and the contact friction force between the roller 2 and the retaining ring on the contact ring 3 may be further adjusted, and various friction situations generated when the roller 2 contacts with the bearing flange in an actual use process may be simulated. By collecting the images of the line contact surface of the oil film when the roller 2 contacts with the retaining ring and does not contact with the retaining ring (that is, the friction force is 0), the data of the friction influence of the retaining ring on the roller 2 under different conditions (different inclination angles of the roller 2 and different contact friction forces between the roller 2 and the retaining ring) are calculated, a range of the simulation experiment of the measuring device is enhanced and the accuracy of the measurement test data is improved.

In an embodiment, the contact ring 3 has a transparent structure, and the image acquisition device is arranged in a central hole of the contact ring 3, and an image acquisition end of the image acquisition device faces the roller 2.

In an embodiment, the image acquisition device includes an imager 4 for acquiring the oil film images on the surface of the roller 2.

Figure 3:
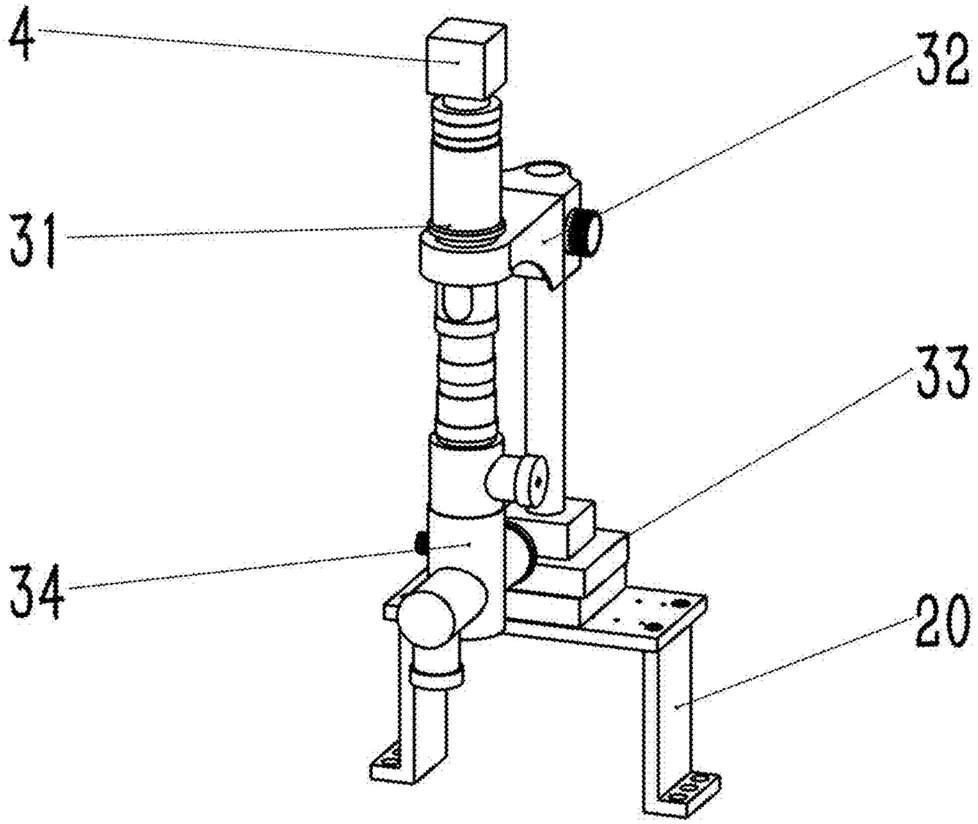
FIG. 3 is a schematic structural diagram of an image acquisition device according to the disclosure.
Figure 4:
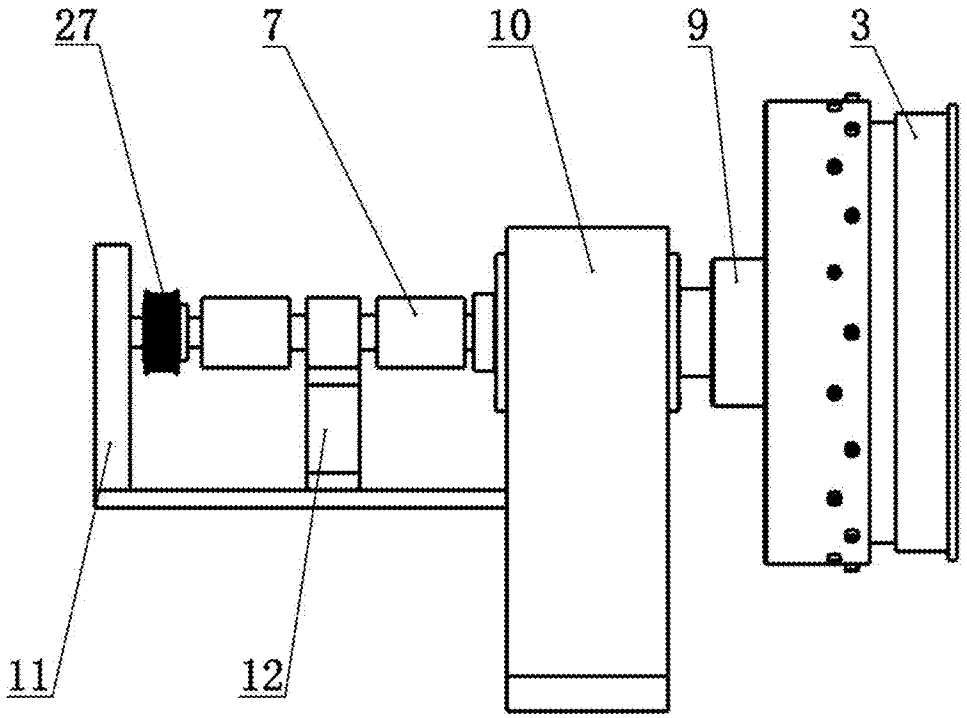
FIG. 4 is a diagram showing a connection relationship between a contact ring and a transmission shaft.

With reference to FIG. 1, FIG. 3 and FIG. 4, the contact ring 3 is made of transparent materials such as sapphire and glass, and a concave central hole is formed in the contact ring 3. When an outer side wall of the contact ring 3 comes into contact with the roller 2 to generate the line contact surface of the oil film, the imager 4 directly moves to an upper part of an detection interval through the central depression of the contact ring 3, and carries out image acquisition and recording perpendicular to the line contact image generated by the roller 2 and the contact ring 3. Therefore, the accuracy of measurement data is improved, and convenient observation of the friction occurrence of the roller 2 may be realized. By recording oil film imaging, an oil film thickness change is obtained, and then the friction torque of roller 2 is calculated.

In an embodiment, the first driving mechanism includes a driving motor 6, a pair of belt pulleys 27, a belt 8 sleeved between the pair of belt pulleys 27, and a transmission shaft 9 arranged on the contact ring 3, where the transmission shaft 9 coincides with an axis of the contact ring 3, and one of the pair of belt pulleys 27 is connected with the driving motor 6, and another of the pair of belt pulleys is connected with the transmission shaft 9.

In an embodiment, the first driving mechanism also includes a transmission shaft seat 10 connected with the transmission shaft 9, and the transmission shaft seat 10 is connected with the other of the pair of belt pulleys 27 through the couplings 7.

Figure 7:
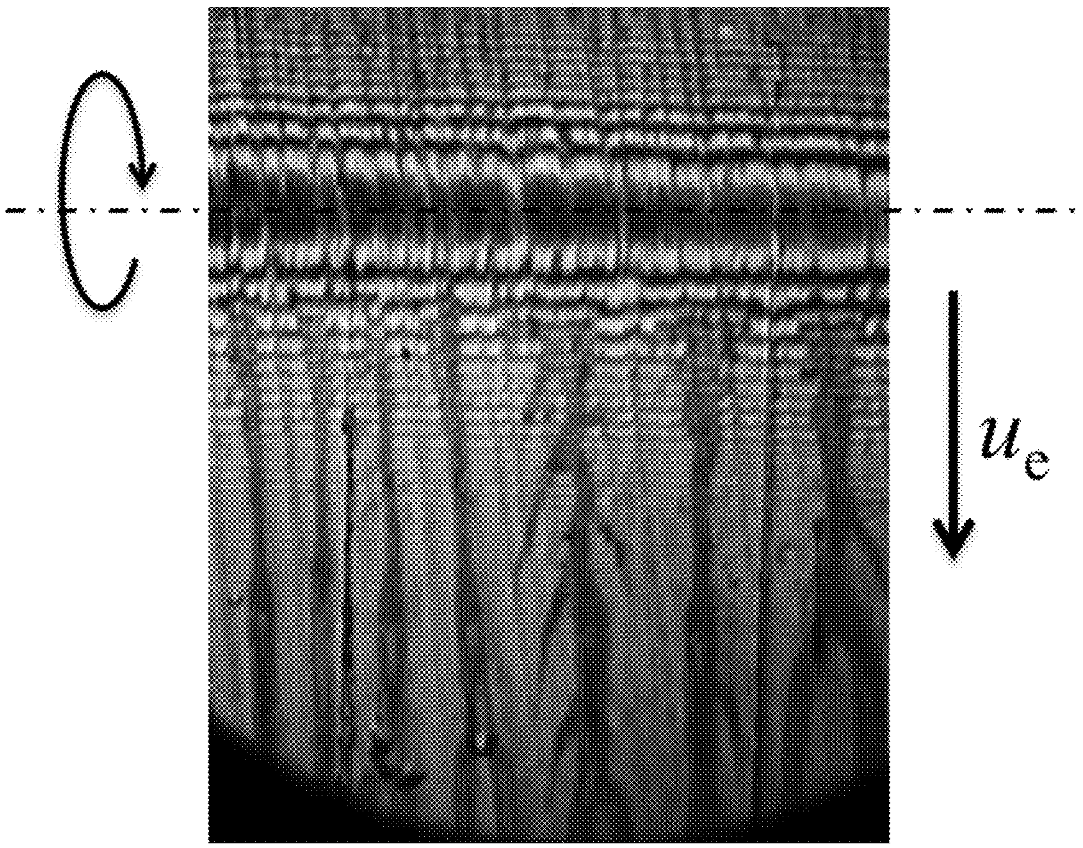
FIG. 7 is a measurement imaging diagram of a roller and the contact ring in a line contact.
Figure 8:
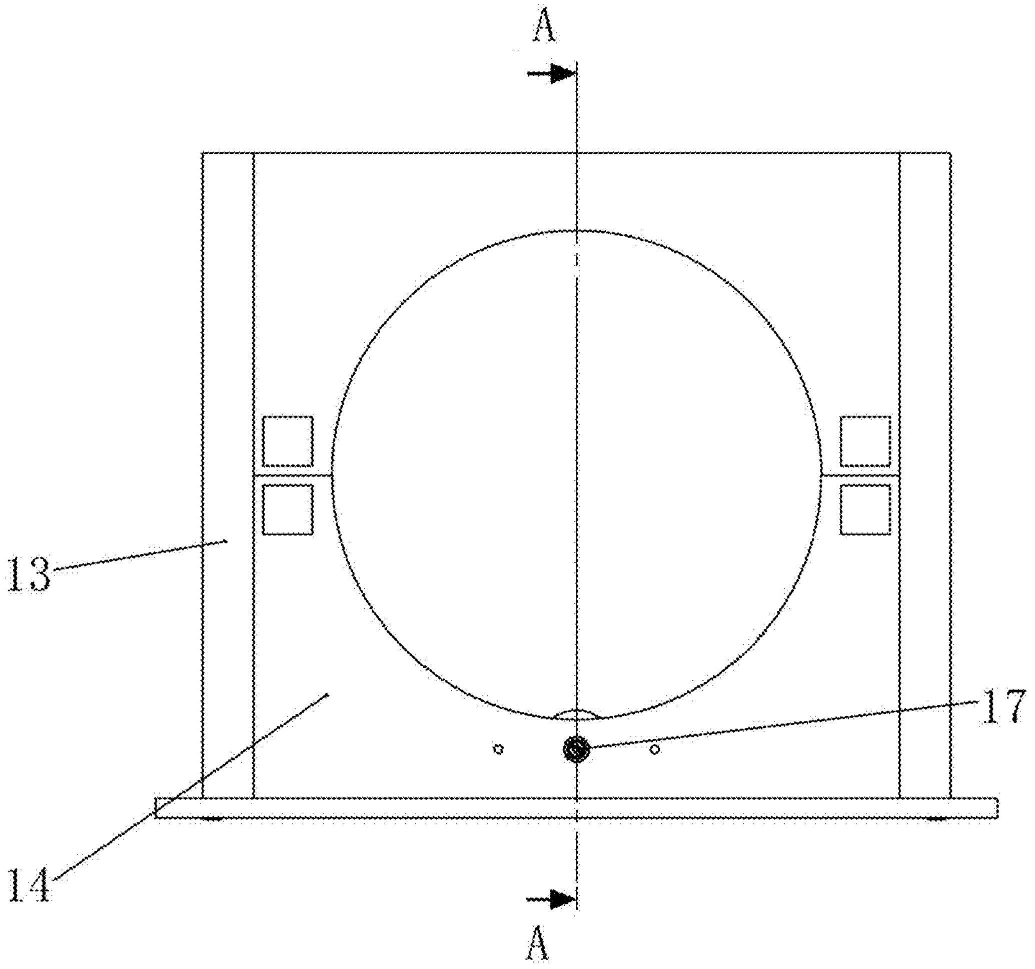
FIG. 8 is a diagram showing a positional relationship between the roller and arc-shaped guide rails.

With reference to FIG. 4 and FIG. 7, a support plate 5 is fixedly connected to the workbench 1, the driving motor 6 is fixedly connected to the support plate 5, an output shaft of the driving motor 6 is in transmission connection with the belt 8 through one of the belt pulleys 27, and one end, away from the driving motor 6, of the belt 8 is sleeved on another belt pulley 27. The axis of the contact ring 3 is fixedly connected with the transmission shaft 9, and the transmission shaft seat 10 is fixedly connected on the workbench 1 corresponding to the transmission shaft 9. The transmission shaft 9 penetrates through the transmission shaft seat 10 and is rotatably connected with the transmission shaft seat 10, and one end of the transmission shaft 9 extending out of the transmission shaft seat 10 is fixedly connected with the adjacent belt pulley 27 through the couplings 7.

By arranging the couplings 7 on the transmission shaft 9 and on both sides of a torque sensor 12 respectively, the couplings 7 are used to buffer and drive the transmission shaft 9 to rotate, so that the contact ring 3 runs stably under the action of the transmission shaft 9 and makes frictional contact with the roller 2, simulating a normal working state of the roller 2. By recording the line contact imaging generated by the contact ring 3 and the roller 2, the friction force acting on the roller 2 during operation is obtained. By recording optical interference measurement results of the line contact surface at a certain speed, and recording changes of optical interference fringes, changes of lubricating oil film thickness and speed may be calculated.

In an embodiment, the second driving mechanism includes an oil cylinder 15, and a driving end of the oil cylinder 15 penetrates through the frame 13 and abuts against the bottom arc-shaped guide rails 14 adjacent to the cylinder 15.

Figure 5:
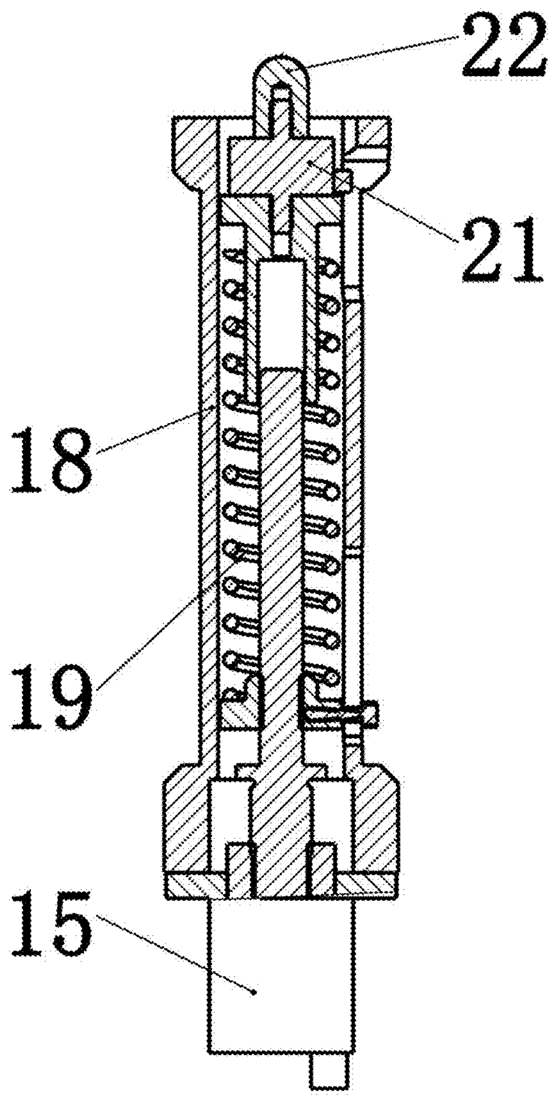
FIG. 5 is a schematic structural diagram of a second driving mechanism.

In this technical scheme, with reference to FIG. 5, FIG. 9 and FIG. 10, the arc-shaped guide rails 14 are slidably connected with the frame 13 in a limited way, and the two arc-shaped guide rails 14 are fixedly connected. The oil cylinder 15 is fixedly connected to a bottom surface of the workbench 1 through a sleeve 18, and the sleeve 18 is sleeved outside an output shaft of the oil cylinder 15, and the sleeve 18 is slidably connected with the output shaft of the oil cylinder 15. By sleeving a support spring 19 on the output shaft of the oil cylinder 15 and fixedly connecting an ejector rod 22 at an end of the support spring 19, only the oil cylinder 15 and the ejector rod 22 need to drive the arc-shaped guide rail 14 at bottom to slide along the frame 13, thereby the contact pressure between the contact ring 3 extending between the inner arc surfaces of the two arc-shaped guide rails 14 and the roller 2 is adjusted, the contact friction force between the roller 2 and the contact ring 3 is controlled, the variability of test conditions is increased and a data acquisition range is improved.

In this technical scheme, a pressure sensor 21 is arranged between the output shaft of the oil cylinder 15 and the ejector rod 22 for detecting a hydraulic acting force provided by the oil cylinder 15 to the roller 2.

In an embodiment, the device also includes a mounting seat 20 fixedly connected to the workbench 1, and the image acquisition device is movably connected to the mounting seat 20.

Figure 6:
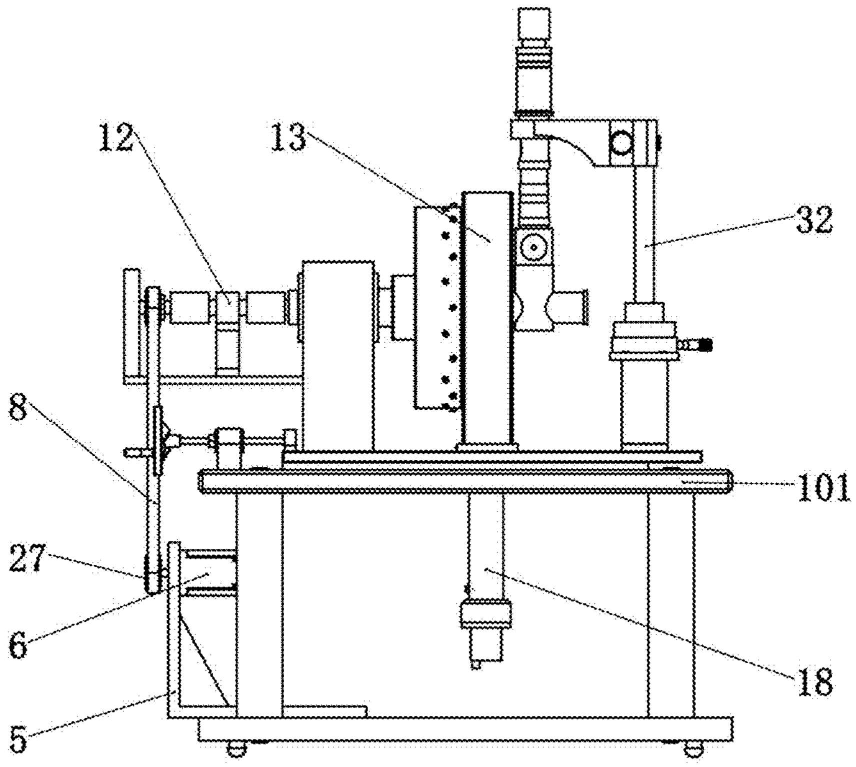
FIG. 6 is a diagram showing a connection relationship between a driving motor and a support plate.

With reference to FIG. 3 and FIG. 6, the mounting seat 20 is fixedly connected to a top surface of the workbench 1, and a movable platform 33 is arranged on a top surface of the mounting seat 20. The movable platform 33 is in the prior art, and will not be described too much. A support frame 32 is fixedly connected to a top surface of the movable platform 33, and a machine body 31 is installed on the support frame 32, and the support frame 32 is a common adjustable lifting structure, specifically including a sliding rod (not labeled in the figure) fixedly connected with the movable platform 33. An adjusting block slides on the sliding rod, and the adjusting block is threadedly connected with a knob. By turning the knob, the sliding or fixing of the adjusting block and the sliding rod is realized, and the three-axis movement of the machine body 31 in the space is realized. A top end of the machine body 31 is installed with the imager 4, and a bottom end of the machine body 31 is connected with a lens converter 34. By moving the machine body 31, the lens converter 34 is driven to extend into the depression in the contact ring 3 to complete the line contact imaging between the roller 2 and the contact ring 3. Moreover, the lens converter 34 may realize the conversion of a shooting angle of the imager 4. When a lens is turned vertically by 90 degrees, the lens converter 34 may be extended inside a ring to measure a film thickness of the line contact. When there is no steering angle, a measuring direction is just aligned with a contact surface between an end surface of the roller and the flange at the front end of the contact ring, so that a film thickness of a contact part between the roller and the flange may be measured. The imager 4 adopts precision high-definition imaging equipment such as a common optical microscope, and the machine body 31 is a charge coupled device (CCD) camera. The above-mentioned movable platform 33 and lens converter 34 are all in the prior art, so we will not make too many statements.

In an embodiment, the workbench 1 includes an upper platform 101 and a lower platform 102, where the upper platform 101 and the lower platform 102 are fixedly connected through brackets 103, and a top surface of the upper platform 101 is slidably connected with a mounting plate 26, and the supporting mechanism is arranged on the mounting plate 26.

Figure 2:
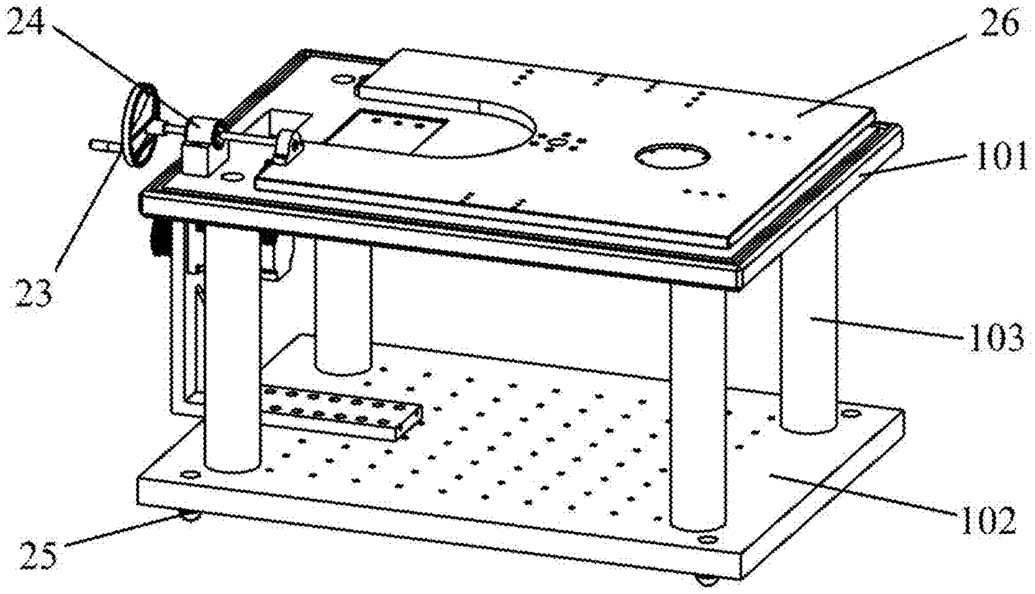
FIG. 2 is a schematic diagram of a workbench according to the disclosure.

With reference to FIG. 1 and FIG. 2, bottom supports 25 are fixedly connected around a bottom of the lower platform 102. The frame 13 is fixedly connected to the mounting plate 26, and the mounting plate 26 is formed with a notch corresponding to the transmission shaft seat 10, so that the mounting plate 26 is slidably connected with the upper platform 101. A screw (not labeled in the figure) penetrates through and is threadedly connected in a threaded seat 24 fixedly connected with the upper platform 101 and arranged on one side of the mounting plate 26. One end of the screw is rotatably fixedly connected with the mounting plate 26 through a bearing, and another end of the screw is fixedly connected with a hand wheel 23, so that the sliding adjustment between the mounting plate 26 and the upper platform 101 may be realized by rotating the screw. In this technical scheme, the oil cylinder 15 is fixedly connected with a bottom surface of the lower platform 102, and a through hole is formed on the mounting plate 26 corresponding to the ejector rod 22 of the oil cylinder 15. When the mounting plate 26 moves to a measurement and test position, the ejector rod 22 corresponds to the position of the through hole, and the frame 13 is arranged at the through hole, so that the ejector rod 22 penetrates through the through hole and extends into the frame 13 to slidably support the arc-shaped guide rails 14.

In a description of the disclosure, it should be understood that terms "longitudinal", "transversal", "up", "down", "front", "back", "left", "right", "vertical", "horizontal", "top", "bottom", "inside", "outside", and orientation or positional relationships indicated are based on orientation or positional relationships shown in accompanying drawings, solely for a convenience of describing the disclosure, rather than indicating or implying that a device or an element referred to must have a specific orientation, be constructed and operated in a specific orientation, therefore it may not be understood as a limitation of the disclosure.

The above-mentioned embodiments only describe preferred modes of the disclosure, and do not limit a scope of the disclosure. Under a premise of not departing from a design spirit of the disclosure, various variations and modifications made by ordinary technicians in the field to the technical scheme of the disclosure shall fall within a protection scope determined by claims of the disclosure.

What is claimed is:

1. A roller lubrication performance measuring and testing device, comprising:

a workbench;

a supporting mechanism comprising a frame and two arc-shaped guide rails arranged in the frame, wherein the frame is arranged on the workbench, the arc-shaped guide rails are slidably matched with the frame, inner arc surfaces of the two arc-shaped guide rails are arranged oppositely, and the two arc-shaped guide rails are fixedly connected;

a roller rotatably connected to a bottom one of the arc-shaped guide rails;

a contact ring arranged between the inner arc surfaces of the two arc-shaped guide rails, wherein an outer surface of the contact ring is used for abutting against a surface of the roller, and a front end of the contact ring is provided with a retaining ring for abutting against a side wall of the roller;

a first driving mechanism, wherein a driving end of the first driving mechanism is connected with the contact ring, and the first driving mechanism is used for driving the contact ring to rotate, so that the contact ring generates friction with the surface of the roller;

a second driving mechanism, wherein a driving end of the second driving mechanism is connected with the bottom one of the arc-shaped guide rails, and the second driving mechanism is used for driving the bottom one of the arc-shaped guide rails to slide relative to the frame so as to adjust pressure between the roller and the outer surface of the contact ring; and an image acquisition device used for acquiring oil film images on the surface of the roller.

2. The roller lubrication performance measuring and testing device according to claim 1, wherein a clamping groove is formed in the bottom one of the arc-shaped guide rails, and the roller is rotatably connected in the clamping groove.

3. The roller lubrication performance measuring and testing device according to claim 2, further comprising a positioning shaft group, wherein an inner wall of the clamping groove is provided with two shaft holes corresponding to the positioning shaft group, wherein the positioning shaft group comprises a positioning shaft penetrating between the two shaft holes, and the roller is rotatably connected with the shaft holes through the positioning shaft, and micro bearings are arranged in the shaft holes corresponding to the positioning shaft, and the micro bearings are used for adjusting an inclination angle of the positioning shaft.

4. The roller lubrication performance measuring and testing device according to claim 1, wherein the contact ring has a transparent structure, and the image acquisition device is arranged in a central hole of the contact ring, and an image acquisition end of the image acquisition device faces the roller.

5. The roller lubrication performance measuring and testing device according to claim 4, wherein the image acquisition device comprises an imager for acquiring the oil film images on the surface of the roller.

6. The roller lubrication performance measuring and testing device according to claim 1, wherein the first driving mechanism comprises a driving motor, a pair of belt pulleys, a belt sleeved between the pair of belt pulleys, and a transmission shaft arranged on the contact ring, wherein the transmission shaft coincides with an axis of the contact ring, and one of the pair of belt pulleys is connected with the driving motor, and an other of the pair of belt pulleys is connected with the transmission shaft.

7. The roller lubrication performance measuring and testing device according to claim 6, wherein the first driving mechanism further comprises a transmission shaft seat connected with the transmission shaft, and the transmission shaft seat is connected with the other of the pair of belt pulleys through couplings.

8. The roller lubrication performance measuring and testing device according to claim 2, wherein the second driving mechanism comprises an oil cylinder, and a driving end of the oil cylinder penetrates through the frame and abuts against the bottom one of arc-shaped guide rails.

9. The roller lubrication performance measuring and testing device according to claim 1, further comprising a mounting seat fixedly connected to the workbench, and the image acquisition device is movably connected to the mounting seat.

10. The roller lubrication performance measuring and testing device according to claim 1, wherein the workbench comprises an upper platform and a lower platform, wherein the upper platform and the lower platform are fixedly connected through brackets, and a top surface of the upper platform is slidably connected with a mounting plate, and the supporting mechanism is arranged on the mounting plate.

* * * * *